US012594367B2

(12) United States Patent
Vartia et al.

(10) Patent No.: US 12,594,367 B2
(45) Date of Patent: Apr. 7, 2026

(54) SYSTEM AND METHOD FOR PRODUCING FLUID FOR PERITONEAL DIALYSIS

(71) Applicant: Gambro Lundia AB, Lund (SE)

(72) Inventors: Christian Vartia, Veberod (SE); Henrik Lindgren, Genarp (SE); Per-Olof Borgqvist, Lund (SE); Olof Jansson, Vellinge (SE)

(73) Assignee: Gambro Lundia AB, Lund (SE)

( * ) Notice: Subject to any disclaimer, the term of this patent is extended or adjusted under 35 U.S.C. 154(b) by 609 days.

(21) Appl. No.: 17/797,952

(22) PCT Filed: Feb. 5, 2021

(86) PCT No.: PCT/EP2021/052787
§ 371 (c)(1),
(2) Date: Aug. 5, 2022

(87) PCT Pub. No.: WO2021/156431
PCT Pub. Date: Aug. 12, 2021

(65) Prior Publication Data
US 2023/0040372 A1 Feb. 9, 2023

(30) Foreign Application Priority Data
Feb. 6, 2020 (SE) .................................... 2050128-4

(51) Int. Cl.
*A61M 1/14* (2006.01)
*A61M 1/16* (2006.01)
*A61M 1/28* (2006.01)
(52) U.S. Cl.
CPC ............ *A61M 1/1672* (2014.02); *A61M 1/14* (2013.01); *A61M 1/1654* (2013.01);
(Continued)

(58) Field of Classification Search
CPC .... A61M 1/14; A61M 1/1654; A61M 1/1672; A61M 1/282; A61M 1/284; A61M 1/287
See application file for complete search history.

(56) References Cited

U.S. PATENT DOCUMENTS 6,666,842 B1 12/2003 Sakai
10,293,094 B2 5/2019 Spanget et al.
(Continued)

FOREIGN PATENT DOCUMENTS

CN 115023248 9/2022
CN 115038473 9/2022
(Continued)

OTHER PUBLICATIONS

"Dialysis Fluid Regeneration by Forward Osmosis: A Feasible Option for Ambulatory Dialysis Systems," Saudi J. Kidney Dis Transpl 2010; 21 (4):748-749 2010—Saudi Center for Organ Transplantation; Saudi Journal of Kidney Diseases and Transplantation.
(Continued)

*Primary Examiner* — John Kim
(74) *Attorney, Agent, or Firm* — K&L Gates LLP

(57) ABSTRACT

A system and method for producing fluid for peritoneal dialysis (PD) is disclosed. The system comprises a fluid path including one or more PD-concentrate connectors each connected to one or more sources of PD-concentrate fluid, and a water connector connected to a source of water. The system further includes a forward osmosis FO-unit including a draw side and a feed side separated by a FO-membrane. The FO-unit is fluidly connected to the fluid path. The FO-unit receives the one or more PD-concentrate fluids at the draw side, and receives the water at the feed side. Purified water is transported to one or more PD-concentrate fluids through the FO-membrane by means of an osmotic pressure gradient between the draw side and the feed side. The transported purified water is further purified by the
(Continued)

FO-membrane and the one or more PD-concentrate fluids is diluted to produce a diluted PD-concentrate fluid.

16 Claims, 5 Drawing Sheets

(52) U.S. Cl.
 CPC ............ *A61M 1/282* (2014.02); *A61M 1/284* (2014.02); *A61M 1/287* (2013.01)

(56) References Cited

U.S. PATENT DOCUMENTS

| | | |
|---|---|---|
| 12,329,888 B2 | 6/2025 | Marterstock et al. |
| 2017/0065762 A1 | 3/2017 | Larsen et al. |
| 2018/0021501 A1 | 1/2018 | Gerber et al. |
| 2023/0103623 A1 | 4/2023 | Marterstock et al. |
| 2023/0146806 A1* | 5/2023 | Marterstock .......... A61M 1/166 210/500.1 |

FOREIGN PATENT DOCUMENTS

| | | |
|---|---|---|
| JP | 2000107286 | 4/2000 |
| JP | 2016-064122 | 4/2016 |
| JP | 6575249 B2 | 4/2016 |
| WO | 2004008826 | 1/2004 |
| WO | 2009083011 | 7/2009 |
| WO | 2021016188 | 1/2021 |
| WO | 20210151874 | 8/2021 |

OTHER PUBLICATIONS

International Search Report—PCT/EP2021/052787 mailed May 6, 2021—4 pages.
Written Opinion—PCT/EP2021/052787 mailed May 6, 2021—9 pages.
Swedish Search Report—Patent Application No. 2050128-4—mailed Sep. 10, 2020—2 pages.
Swedish SHS IP Office Communication dated Jan. 20, 2025—10 pages.

* cited by examiner

SYSTEM AND METHOD FOR PRODUCING FLUID FOR PERITONEAL DIALYSIS

PRIORITY CLAIM

This application is a national phase entry of PCT/EP2021/052787, filed Feb. 5, 2021, which claims priority to Swedish Patent Application No. 2050128-4, filed Feb. 6, 2020, the entire disclosures of which are incorporated by reference herein.

TECHNICAL FIELD

The present invention relates to the field of peritoneal dialysis, and to systems and methods for producing fluid to be used in peritoneal dialysis.

BACKGROUND

Peritoneal dialysis (PD) is a method for treating patients suffering from renal failure. During PD, the peritoneal cavity of a patient is filled with fresh PD-fluid, and waste and fluid is transported from the blood of the patient via the peritoneum to the PD-fluid. The used PD-fluid is thereafter drained from the patient.

There are several kinds of PD. In automated peritoneal dialysis, APD, a machine is used to fill the peritoneal cavity with fresh PD-fluid, and after a specific dwell time, the machine drains the used PD solution from the body. This procedure is repeated several times, typically during night. In continuous flow peritoneal dialysis (CFPD) for example, a machine is used to provide a continuous flow of fresh PD-fluid to the peritoneal cavity of the patient, and a continuous flow of used PD-fluid from the patient. APD systems on the market today use centrally manufactured PD-fluids that are shipped to the patient ready to use in bags, which are stored in the patient's home.

Transportation of PD-fluids adds treatment cost and has a negative impact on the environment. The storage of PD-fluids in the patient's home is space demanding. Patient handling of the PD-fluids prior to the treatment adds to the patient burden, wherein many patients find it heavy to place the PD-fluid bags in correct position before the start of treatment.

There is accordingly a need to reduce the negative consequences listed above.

SUMMARY

It is an objective of the disclosure to alleviate at least some of the drawbacks with the prior art. It is a further objective to provide a cost-efficient solution for producing fluid for PD at the point of care. It is still a further objective to provide a compact solution for producing fluid for PD at the point of care. It is yet a further objective to provide a PD-fluid solution that consumes low amounts of water.

These objectives and others are at least partially achieved by the system and method according to the independent claims, and by the embodiments according to the dependent claims.

According to one aspect of the present disclosure, which may be combined with any other aspect or portion thereof, the disclosure relates to a system for producing fluid for peritoneal dialysis (PD). The system includes a fluid path comprising one or more PD-concentrate connectors each configured to be connected to one or more sources of PD-concentrate fluid, and a water connector configured to be connected to a source of water. The system further comprises a forward osmosis- (FO-) unit comprising a draw side and a feed side separated by a FO-membrane, the FO-unit being fluidly connected to the fluid path. The FO-unit is configured to receive the one or more PD-concentrate fluids at the draw side, and to receive the water at the feed side to transport purified water from the water to the one or more PD-concentrate fluids through the FO-membrane by means of an osmotic pressure gradient between the draw side and the feed side. The one or more PD-concentrate fluids is thereby diluted to produce a diluted PD-concentrate fluid. The proposed system can purify water at the same time as diluting the PD-concentrates, whereby water purification may be made less complex and less costly. In an embodiment, the transported purified water is further purified by the FO-membrane of the FO-unit.

According to another aspect of the present disclosure, which may be combined with any other aspect or portion thereof, the system comprises a concentration sensor configured to sense a concentration of the diluted PD-concentrate fluid, and a control arrangement configured to control a degree of dilution of the one or more PD-concentrates during production of diluted PD-concentrate fluid based on the sensed concentration such that one or more predetermined criteria are fulfilled.

According to another aspect of the present disclosure, which may be combined with any other aspect or portion thereof, the one or more predetermined criteria comprises: the concentration of the diluted PD-concentrate fluid having a concentration that is equal to, or close to (e.g., that is at least substantially equal to), a concentration that matches a prescribed concentration of the diluted PD-fluid in a final PD-fluid; the concentration of the diluted PD-concentrate fluid corresponding to a final degree of dilution for a PD-fluid; and/or the concentration of the diluted PD-concentrate fluid being within a concentration interval for a certain time.

According to another aspect of the present disclosure, which may be combined with any other aspect or portion thereof, the control arrangement is configured to control the degree of dilution of the one or more PD-concentrates by controlling the flow rate of the one or more PD-concentrate fluids to an inlet of the draw side, and/or controlling the flow rate of water to an inlet of the feed side, and/or controlling the flow rate of reject water from an outlet of the feed side.

According to another aspect of the present disclosure, which may be combined with any other aspect or portion thereof, the system comprises a container fluidly connected or connectable to the fluid path, wherein the container is arranged to receive the diluted PD-concentrate fluid.

According to another aspect of the present disclosure, which may be combined with any other aspect or portion thereof, the fluid path comprises a first recirculation fluid path including the draw side of the FO-unit and the container. The control arrangement is configured to control the degree of dilution by recirculating the diluted concentrate fluid in the first recirculation fluid path until the one or more predetermined criteria are fulfilled.

According to another aspect of the present disclosure, which may be combined with any other aspect or portion thereof, the system includes a pump positioned and arranged to at least one of (i) deliver the diluted PD-concentrate fluid to or (ii) remove the diluted PD-concentrate fluid from the container along a line.

According to another aspect of the present disclosure, which may be combined with any other aspect or portion thereof, the system includes at least one of (i) a fluid heater located along the line, (ii) a concentrate pump located in the recirculation fluid path, wherein the concentrate pump is optionally placed in parallel fluidically with a valve or (iii) an air/fluid sensor located in the recirculation fluid path for determining when PD-concentrate fluid has reached the sensor.

According to another aspect of the present disclosure, which may be combined with any other aspect or portion thereof, the fluid path comprises a second recirculation fluid path including the feed side of the FO-unit, wherein the control arrangement is configured to recirculate the water in the second recirculation fluid path until the one or more predetermined criteria are fulfilled.

According to another aspect of the present disclosure, which may be combined with any other aspect or portion thereof, the control arrangement is configured to direct the diluted PD-concentrate fluid to an outlet connector upon one or more predetermined criteria being fulfilled.

According to another aspect of the present disclosure, which may be combined with any other aspect or portion thereof, the system comprises a water container configured to collect the water downstream the FO-unit.

According to another aspect of the present disclosure, which may be combined with any other aspect or portion thereof, the fluid path comprises an osmotic agent connector configured to be connected to a source of osmotic agent, and wherein the control arrangement is configured to supply osmotic agent from the source of osmotic agent to the fluid path to achieve a prescribed concentration of the osmotic agent in the diluted PD-concentrate fluid.

According to another aspect of the present disclosure, which may be combined with any other aspect or portion thereof, the fluid path comprises an inlet connector configured to be connected to a source of effluent. The FO-unit is configured to receive the effluent at the feed side to transport water from the effluent to the one or more PD-concentrate fluids through the FO-membrane by means of an osmotic pressure gradient between the draw side and the feed side. The one or more PD-concentrate fluids are thereby diluted to produce a pre-diluted PD-concentrate fluid, wherein the pre-diluted concentrate fluid is included in the one or more PD-concentrate fluids that the FO-unit is configured to receive.

According to another aspect of the present disclosure, which may be combined with any other aspect or portion thereof, the system comprises an effluent container fluidly connected or connectable to the fluid path, wherein the container is arranged to receive the effluent from the patient.

According to another aspect of the present disclosure, which may be combined with any other aspect or portion thereof, the system comprises a pretreatment unit configured to pretreat the water received via the water connector before it is passed to the FO-unit.

According to a further aspect of the present disclosure, which may be combined with any other aspect or portion thereof, the disclosure comprises a method for producing fluid for peritoneal dialysis (PD) in a system comprising a forward osmosis (FO) unit. The FO-unit comprises a draw side and a feed side separated by a FO-membrane. The FO-unit is configured to receive one or more PD-concentrate fluids at the draw side, and to receive the water at the feed side, to transport purified water from the water to the one or more PD-concentrate fluids through the FO-membrane by means of an osmotic pressure gradient between the draw side and the feed side and thereby dilute the one or more PD-concentrate fluids into a diluted PD-concentrate fluid. The method comprises directing the water into the feed side of the FO-unit, and directing the one or more PD-concentrate fluids into the draw side.

According to another aspect of the present disclosure, which may be combined with any other aspect or portion thereof, the method comprises sensing a concentration of the diluted PD-concentrate fluid, and controlling the degree of dilution of the one or more PD-concentrates during production of diluted PD-concentrate fluid based on the sensed concentration such that one or more predetermined criteria are fulfilled.

According to another aspect of the present disclosure, which may be combined with any other aspect or portion thereof, the one or more predetermined criteria comprises: the concentration of the diluted PD-concentrate fluid having a concentration that is equal to, or close to (e.g., that is at least substantially equal to), a concentration that matches a prescribed concentration of the diluted PD-fluid in a final PD-fluid; the concentration of the diluted PD-concentrate fluid corresponding to a final degree of dilution for a PD-fluid; and/or the concentration of the diluted PD-concentrate fluid being within a concentrate interval for a certain time.

According to another aspect of the present disclosure, which may be combined with any other aspect or portion thereof, the method comprises controlling the degree of dilution of the one or more PD-concentrates by controlling the flow rate of the one or more PD-concentrate fluids to an inlet of the draw side, and/or controlling the flow rate of water at an inlet of the feed side, and/or controlling the flow rate of reject water from an outlet of the feed side.

According to another aspect of the present disclosure, which may be combined with any other aspect or portion thereof, the method comprises directing the diluted PD-concentrate fluid into a container.

According to another aspect of the present disclosure, which may be combined with any other aspect or portion thereof, the method comprises controlling the degree of dilution by recirculating the diluted concentrate fluid in a first recirculation fluid path including the draw side of the FO-unit and the container, until the one or more predetermined criteria are fulfilled.

According to another aspect of the present disclosure, which may be combined with any other aspect or portion thereof, the method comprises controlling the degree of dilution by recirculating the water in a second recirculation fluid path including the feed side of the FO-unit until the one or more predetermined criteria are fulfilled.

According to another aspect of the present disclosure, which may be combined with any other aspect or portion thereof, the method comprises directing used water downstream the FO-unit to a water container.

According to another aspect of the present disclosure, which may be combined with any other aspect or portion thereof, the method comprises supplying an osmotic agent from a source of the osmotic agent to the fluid path to achieve a prescribed concentration of the osmotic agent in the diluted PD-concentrate fluid.

According to another aspect of the present disclosure, which may be combined with any other aspect or portion thereof, the method comprises directing effluent from a source of effluent to the feed side of the FO-unit to transport water from the effluent to the one or more PD-concentrate fluids through the FO-membrane by means of an osmotic pressure gradient between the draw side and the feed side. The one or more PD-concentrate fluids are thereby diluted to produce a pre-diluted PD-concentrate fluid, wherein the pre-diluted concentrate fluid is included in the one or more PD-concentrate fluids that the FO-unit is configured to receive.

According to another aspect of the present disclosure, which may be combined with any other aspect or portion thereof, the method comprises pretreating the water received via the water connector before it is passed to the FO-unit.

According to another aspect of the present disclosure, which may be combined with any other aspect or portion thereof, the method comprises directing the diluted PD-concentrate fluid to an outlet container upon one or more predetermined criteria are being fulfilled.

According to another aspect of the present disclosure, which may be combined with any other aspect or portion thereof, one of the one or more PD-concentrate sources comprises a fluid, including one or more of: lactate, acetate, citrate, bicarbonate, NaCl, MgCl2, CaCl2) and KCl.

According to yet another aspect of the present disclosure, which may be combined with any other aspect or portion thereof, the disclosure relates to a computer program comprising instructions to cause the system according to the any system aspect to execute the steps of the method according to any method aspect.

According to yet a further aspect of the present disclosure, which may be combined with any other aspect or portion thereof, the disclosure relates to a computer-readable memory having stored thereon the computer program of the computer aspect.

Additional features and advantages are described in, and will be apparent from, the following Detailed Description and the Figures. The features and advantages described herein are not all-inclusive and, in particular, many additional features and advantages will be apparent to one of ordinary skill in the art in view of the figures and description. Also, any particular embodiment does not have to have all of the advantages listed herein and it is expressly contemplated to claim individual advantageous embodiments separately. Moreover, it should be noted that the language used in the specification has been selected principally for readability and instructional purposes, and not to limit the scope of the inventive subject matter.

DETAILED DESCRIPTION

In the following disclosure, several embodiments of systems and methods for producing fluids for PD are described. The embodiments each make use of a forward osmosis (FO) unit to dilute one or more PD-concentrates using purified water transported over a FO-membrane from water. The water becomes purified when it is transported over the FO-membrane, and directly dilutes the PD-concentrate on the other side of the FO-membrane into a diluted PD-concentrate fluid. The diluted PD-concentrate may be recirculated until it has pulled enough water through the FO membrane to reach a desired dilution. The diluted PD-concentrate may have a prescribed composition of a final PD-fluid after the FO-session or may need to be mixed with additional PD-concentrates, e.g., a PD-fluid comprising an osmotic agent, before it has the prescribed composition of a PD-fluid. A PD-fluid may be defined as a PD-fluid that is ready to be used by a patient in a PD-treatment. The system may be used for different variants of automated PD, including on-line mixing of PD-fluid and batch-wise mixing of PD-fluid. The water may be pre-treated before it is used in FO-unit 6.

The water that is used in the FO-unit may be raw water (e.g. tap water) or pre-treated raw water. The systems described herein may include a pretreatment module that is arranged to treat the raw water before it is provided to the FO-unit.

Figure 1:
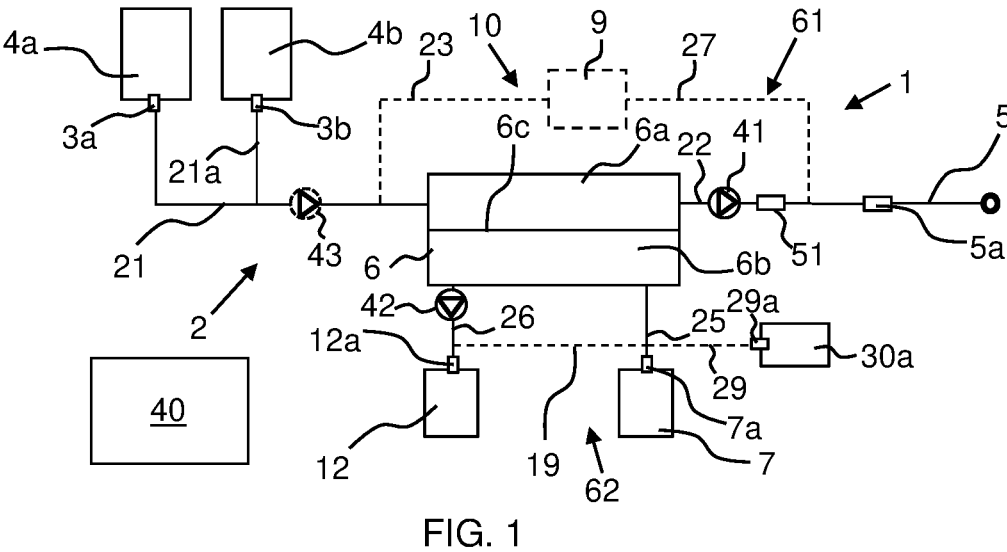
FIGS. 1 and 4 to 9 illustrate systems for producing fluid for PD according to some embodiments.

In the following a system for producing fluids for PD is described with reference to FIG. 1. References that are the same throughout the figures will generally not be repeated. The system 1 comprises a fluid path 2, a plurality of connectors and a forward osmosis (FO)-unit 6. The fluid path 2 may be enclosed inside an enclosure (not shown in FIG. 1). The fluid path 2 may be part of an apparatus. The fluid path 2 comprises a plurality of fluid lines. These fluid lines may be a plurality, or all of the fluid lines as described herein. The connectors include one or more PD-concentrate connectors 3a, 3b. Each PD-concentrate connector 3a, 3b is configured to be connected to a source of PD-concentrate fluid 4a, 4b. A source of PD-concentrate fluid is typically a bag with PD-concentrate. Each PD-concentrate connector 3a, 3b is then configured to be connected to a corresponding connector provided with the bag of PD-concentrate fluid. The connectors also include a water connector 7a. The water connector 7a may be a water port. The water connector 7a is typically configured to be connected to a source of raw water, for example, a hose that is connected to a tap. The raw water may thus be tap water. The water may be pretreated before it is supplied to the FO-unit 6.

The system 1 may also comprise a pretreatment unit (8, FIGS. 4 to 8) configured to pretreat the water received via the water connector 7a before it is passed to the FO-unit 6. The FO-unit 6 comprises a draw side 6a and a feed side 6b separated by a FO-membrane 6c. The FO-membrane 6c typically has a pore-size in the nanometer (nm) range, for example from 0.5 to 5 nm or less depending on the solutes that are intended to be blocked. The FO-unit 6 is fluidly connected to the fluid path 2. The FO-unit 6 is configured to receive the one or more PD-concentrate fluids 4a, 4b at the draw side 6a and to receive the (pretreated) water at the feed side 6b to transport purified water from the water to the one or more PD-concentrate fluids through the FO-membrane 6c by means of an osmotic pressure gradient between the draw side 6a and the feed side 6b. The one or more PD-concentrate fluids are thereby diluted into a diluted PD-concentrate fluid. Suitable FO-units for FO-unit 6 may be provided by Aquaporin™, AsahiKASEI™, Berghof™, CSM™, FTSH₂O™, Koch Membrane Systems™, Porifera™, Toyobo™ and Toray™.

The FO-membrane 6c may be a water permeable membrane, which separates the water (feed side) and the PD-concentrate (draw side). The fluids in the different sides 6a, 6b may flow in counter-current or co-current flows. The water may flow single-pass, thus, the used water may be passed to drain after having passed through the feed side 6b once. Again, the FO-membrane 6c may have a pore-size in the nanometer (nm) range, for example from 0.5 to 5 nm or less depending on the solutes that are intended to be blocked. The FO-membrane 6c is typically designed to be more or less exclusively selective towards water molecules, which enables the membrane to separate water, and thus be further purified, from all other contaminants. The geometry of the membrane may be flat-sheet, tubular or hollow fiber. Alternatively, the water may be recirculated to the feed side 6b one or more time and/or the draw side fluid may be recirculated to the draw side 6a one or more time. Purified water from the water is transported over the FO-membrane 6c by means of the driving force created by the osmotic pressure difference between the water (feed solution) and the one or more PD-concentrate fluids (draw solution). This means that the water will become more concentrated throughout the FO process. The one or more PD-concentrates will on the other hand be more and more diluted throughout the FO process. The FO-membrane 6c may be a water treatment membrane capable of facilitating the forward osmosis process. It is a semipermeable membrane that allows a flow of water from the low concentrate side (feed side) to the high concentrate side (draw side). The FO-membrane typically comprises a thin rejection layer (or active layer) and an underlying porous support. The geometry of the membrane may be flat-sheet, tubular or hollow fiber.

In more detail, a first PD-concentrate bag 4a is connected via a first bag connector (not shown) to the first PD-concentrate connector 3a. A first fluid line 21 is fluidly connected between the first PD-concentrate connector 3a and an inlet port of the draw side 6a. The first fluid line 21 thus connects the first PD-concentrate connector 3a and the draw side 6a. A second PD-concentrate bag 4b is connected via a second bag connector (not shown) to a second PD-concentrate connector 3b. A fluid line 21a is fluidly connected between the second PD-concentrate connector 3b and the first fluid line 21. The fluid line 21a thus connects the second PD-concentrate connector 3b and the first fluid line 21. The fluid path 2 thus comprises the second PD-concentrate connector 3b. The second PD-concentrate connector 3b is configured to be connected to a source of fluid containing osmotic agent. The fluid line 21a may alternatively be connected to the second fluid line 22 to supply PD-concentrate from the second PD-fluid bag 4b to the diluted PD-fluid.

A second fluid line 22 is fluidly connected between an outlet of the draw side 6a and an outlet connector 5a. The outlet connector 5a is for example an outlet port. The second fluid line 22 thus fluidly connects the draw side 6a and the outlet connector 5a. The outlet connector 5a is configured to be connected to a corresponding connector (not shown) of a fluid line 5 configured to transport final PD-fluid directly to a catheter of patient, to a cycler for pumping the fluid to a patient, or to a batch container. A first pump 41 is configured to control a flow rate of the diluted PD-concentrate fluid in the second fluid line 22. At the same time, the first pump 41 may control (if pump 43 is not provided) a flow rate of PD-concentrate fluid in the first fluid line 21. In some embodiments, a third pump 43 is arranged to control a flow rate of the one or more PD-concentrate fluids in the first fluid line 21, and thus to the draw side 6a or to a container 9, if present. The container 9 is explained further below. A third fluid line 25 is connected between the water connector 7a and an inlet port of the feed side 6b. The third fluid line 25 thus fluidly connects the water connector 7a and the feed side 6b. A fourth fluid line 26 is connected between an outlet port of the feed side 6b and a drain connector 12a. Thus, the fourth fluid line 26 connects the feed side 6b and the drain connector 12a. A second pump 42 is arranged to control a flow rate of reject water from the feed side 6b. The second pump 42 is in the illustrated embodiment arranged to operate with the fourth fluid line 26. The drain connector 12a is configured to be connected to a corresponding connector of a drain line (not shown), which may be connected to a drain to remove the reject water after use, or to a bag or water container 12 for used water. Thus, in some embodiments, the system 1 comprises a water container 12 configured to collect the used water downstream the FO-unit 6. The used water may be used as feed solution in an upcoming FO-session, e.g., during a first part of the FO-session, so that water consumption is reduced.

A concentration sensor 51 is arranged to sense a concentration of the fluid in the second fluid line 22. The concentration sensor 51 is thereby positioned to sense a concentration of the diluted PD-concentrate fluid. In some embodiments, the system 1 comprises a container 9. The container 9 is fluidly connected or connectable to the fluid path 2. The container 9 is arranged to receive the diluted PD-concentrate fluid. The container 9 may also be used to collect the one or more concentrates before supplying to the draw side 6a. A variant embodiment is to prefill one or more concentrates in container 9 for mixing to form a batch, which may be a batch for the entire treatment. Additional concentrates may then be added after the dilution process. In embodiments comprising the container 9, a fifth fluid line 27 is fluidly connected between the second fluid line 22 downstream of the concentration sensor 41 and the container 9. The fifth fluid line 27 thus fluidly connects the second fluid 22 and the container 9. A sixth fluid line 23 is connected between the container 9 and the first fluid line 21. The sixth fluid line 23 thus fluidly connects the container 9 and the first fluid line 21. The draw side 6a, part of the second fluid line 22, the fifth fluid line 27, the container 9, the sixth fluid line 23 and part of the first fluid line 21 in the illustrated embodiment form a first recirculation fluid path 61. Thus, the fluid path 2 comprises the first recirculation fluid path 61 including the draw side 6a of the FO-unit 6 and the container 9. The control arrangement 10 is configured to control the degree of dilution by recirculating the diluted concentrate fluid in the first recirculation fluid path 61 until one or more predetermined criteria are fulfilled.

Concentration sensor 51 is for example a conductivity sensor configured to sense the conductivity of a fluid, or a resistivity sensor configured to sense the resistivity of a fluid. Even if, e.g., a resistivity sensor is used, the sensed value may be transformed into a conductivity value, if desired and as known in the art. Conductivity may likewise be transformed into resistivity.

In some embodiments, the system 1 comprises a seventh fluid line 19 arranged between the third fluid line 25 and the fourth fluid line 26. The seventh fluid line 19 thus connects the third fluid line 25 and the fourth fluid line 26. The feed side 6b, part of the third fluid line 25, part of the fourth fluid line 26 and the seventh fluid line 19 are included in a second recirculation fluid path 62. Thus, the fluid path 2 in the illustrated embodiment forms a second recirculation fluid path 62 including the feed side 6b of the FO-unit 6a. The control arrangement 10 is configured to recirculate the water in the second recirculation fluid path 62 until one or more predetermined criteria are fulfilled. The water to be circulated may be collected in an additional container (not shown), and water to and from the additional container and the second recirculation path 62 may be passed via one or two ports in the additional container. Additional valves (not shown) may be arranged to control the flow of water into and out of the additional container.

In some embodiments, effluent, i.e., used PD-fluid from a patient, is used as a feed solution before water is used as feed solution. The FO-unit 6 is then configured to receive the effluent at the feed side 6b. Water is transported from the effluent to the one or more PD-concentrate fluids through the FO-membrane 6 by means of an osmotic pressure gradient between the draw side 6a and the feed side 6b and thereby dilutes the one or more PD-concentrate fluids to produce a pre-diluted PD-concentrate fluid. The pre-diluted PD-concentrate fluid is collected in the container 9. The pre-diluted concentrate fluid is then one of the one or more PD-concentrate fluids that the FO-unit 6 is configured to receive. Thus, the one or more PD-concentrates may be pre-diluted with water withdrawn from effluent via FO before they are further diluted with purified water from raw water or pre-treated water. Additional water is thereby saved. In such embodiments, the fluid path 2 may comprise an inlet connector 29a. An eighth fluid line 29 is connected between the inlet connector 29a and the third fluid line 25. The eighth fluid line 29 fluidly connects the inlet connector 29a and the third fluid line 25. The inlet connector 29a is connected to a corresponding connector (not shown) attached to a source of effluent 30a. The source of effluent 30a may be an effluent container or bag with effluent from a previous drain of effluent from a PD-patient. Thus, in some embodiments, the fluid path 2 comprises an inlet connector 29a configured to be connected to a source of effluent 30a, e.g., an effluent container. In some embodiments, the system comprises an effluent container fluidly connected or connectable to the fluid path 2. The effluent container is arranged to receive the effluent from the patient.

The system 1 further comprises a control arrangement 10. The control arrangement 10 comprises a control unit 40 comprising a processor and a memory. The memory typically stores a program, which when executed by the processor controls the system 1. The control unit 40 may also comprise a communication interface enabling the control unit 40 to communicate data and signals to and from components of the system 1, for example sending control signals to valves and pumps, and receiving sensed data from concentration sensors and feedback signals from the valves and pumps. The control arrangement 10 may also comprise any one or more of the illustrated pumps 41, 42, 43. The control arrangement 10 may also include valves that are not included in FIG. 1 for ease of illustration. A valve as described herein is typically an on/off valve and may be a two- or three-way valve.

In some embodiments, the control arrangement 10 is configured to control a degree of dilution of the one or more PD-concentrates during production of diluted PD-concentrate fluid based on the sensed concentration of the diluted PD-fluid, such that one or more predetermined criteria are fulfilled. Depending on the current phase in the production of the PD-fluid, there may be different criteria used, which are explained in more detail below. In some embodiments, the control arrangement 10 is configured to control the degree of dilution of the one or more PD-concentrates by controlling the flow rate of the one or more PD-concentrate fluids to an inlet of the draw side 6a, and/or controlling the flow rate of water to an inlet of the feed side 6b, and/or controlling the flow rate of reject water from an outlet of the feed side 6b. The flow rate of the one or more PD-concentrate fluids to the inlet of the draw side 6a may be controlled with the first pump 41. The flow rate of water to the inlet of the feed side 6b may be controlled with the second pump 42. Any one or more of pumps 41 to 43, and any other pump described herein, are for example volumetric pumps such as piston or membrane pumps. Any one or more of pumps 41 to 43, and any other pump described herein, may alternatively be a flow pump used in operation with a flow meter or weigh scale.

In some embodiments, only one first kind of PD-concentrate is used as a draw solution. The PD-concentrate then includes for example buffer agents. Another second kind of PD-concentrate may then be supplied to the diluted PD-concentrate after the FO-session. The other second kind of PD-concentrate includes for example an osmotic agent. The other second kind of PD-concentrate is for example glucose. Alternatively, the other second kind of PD-concentrate is used as draw solution together with the first kind of PD-concentrate. Thus, the control arrangement 10 is configured to supply osmotic agent from the source of osmotic agent 4b to the fluid path 2 to achieve a prescribed concentration of the osmotic agent in the diluted PD-concentrate fluid.

The diluted PD-concentrate may be recirculated in the first recirculation fluid path 61 until the sensed concentration fulfills one or more criteria for final PD-fluid. Typically, the sensed concentration should be within a certain interval. When this is achieved, the control arrangement 10 is configured to direct the diluted PD-concentrate fluid to an outlet connector 5a. Another criterion is for example that the PD-fluid is ready-made and a certain time is due.

The final PD-fluid has a composition of PD-concentrates and water that achieves a prescribed or predetermined composition. It is thus also known, thus prescribed, which concentration of the one or more PD-concentrates the final PD-fluid should have, such as, 1.36%, 2.27% or 3.86% glucose. The final PD-fluid is PD-fluid that is ready to be delivered to the peritoneal cavity of a patient. The production rate may be batch-wise, that is, a certain volume of final PD-fluid should be produced. The certain volume is then a batch. Alternatively, the production of final PD-fluid is continuous, which is delivered until control arrangement 10 determines that delivery should stop.

One of the one or more PD-concentrate sources 4a may comprise a fluid, including one or more of: lactate, acetate, citrate, bicarbonate, KCl, MgCl2, CaCl2) and NaCl. For example, the PD-concentrate source comprises a fluid containing buffer agents, e.g., one or more of: lactate, citrate, acetate and bicarbonate. This fluid, when diluted with water and possibly other PD-concentrates becomes the final PD-fluid which has a pH applicable for PD treatment, and one or more of: KCL, MgCl2, CaCl2), NaCl.

Figure 2:
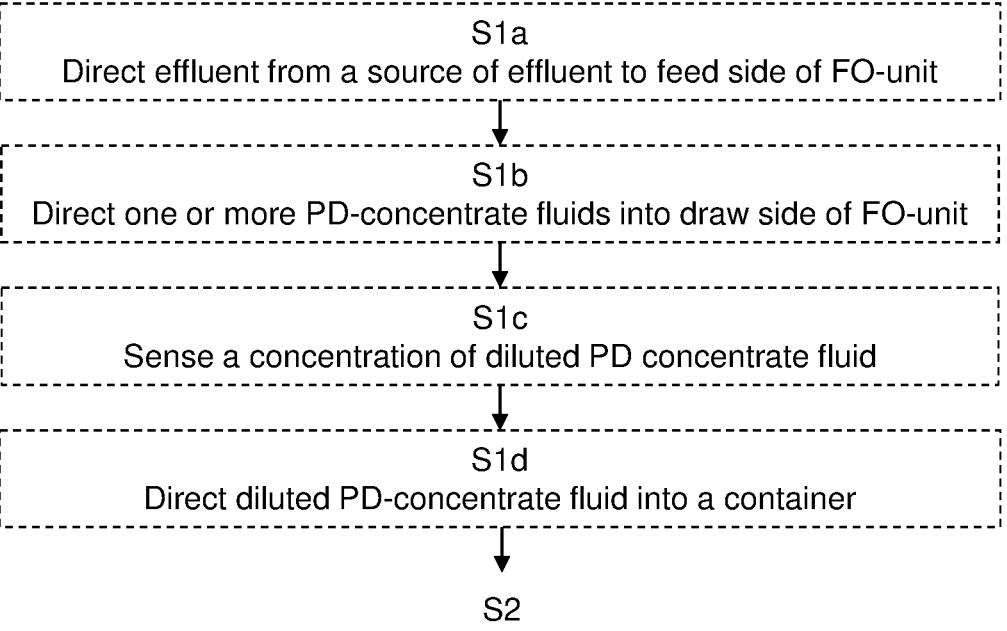
FIGS. 2 and 3 are flowcharts illustrating methods for producing fluid for PD according to some embodiments.
Figure 3:
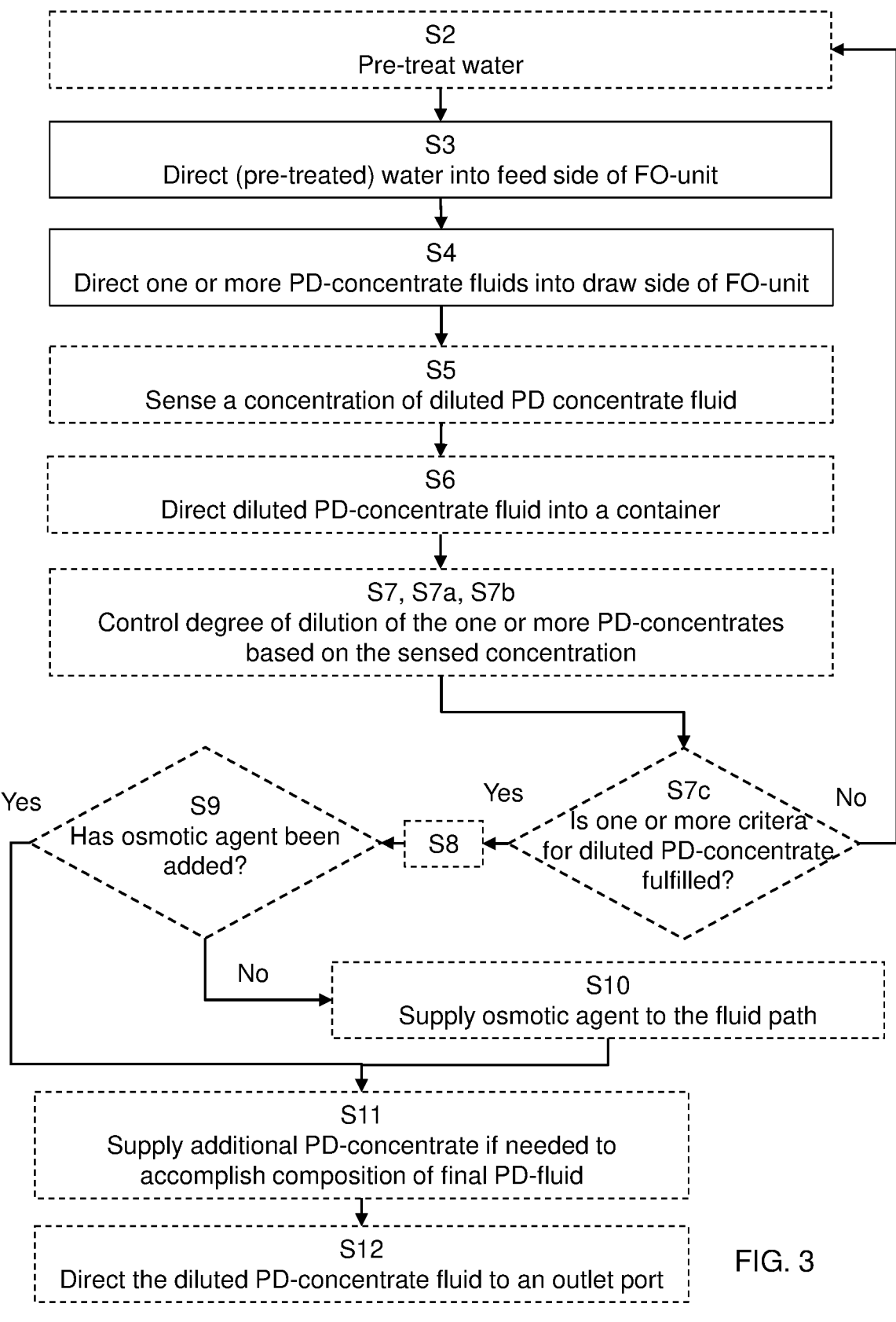

FIG. 2 is a flow chart of a method to produce a pre-diluted PD-fluid by means of effluent and one or more PD-concentrates, according to some embodiments. FIG. 3 is a flow chart of a method to produce fluids for PD, according to some embodiments escribed herein. The methods may be implemented as instructions on a computer program and saved in the memory of the control unit 40. The methods are explained together with the flow charts of FIGS. 2 and 3. The boxes illustrated in dashed line correspond to alternative or optional functions or procedures.

With reference to FIG. 2, the method at S1*a* comprises directing effluent from a source of effluent 30a to the feed side 6b of the FO-unit 6a. The method at S1*b* also comprises directing the one or more PD-concentrate fluids into the draw side 6a. Water from the effluent will then be transported from the effluent to the one or more PD-concentrate fluids through the FO-membrane 6 by means of an osmotic pressure gradient between the draw side 6a and the feed side 6b to thereby dilute the one or more PD-concentrate fluids and produce a pre-diluted PD-concentrate fluid. The pre-diluted concentrate fluid is thereafter included in the one or more PD-concentrate fluids that the FO-unit 6 is configured to receive. In one embodiment, the one or more PD-concentrates used as draw solution includes a PD-concentrate fluid that comprises one or more buffer agents.

The method at S1*c* further comprises sensing a concentration of the diluted PD-concentrate fluid, for example with the concentrate sensor 51. The method also comprises directing S1d the diluted PD-concentrate fluid into the container 9. Thus, the PD-concentrate may be pre-diluted using effluent from a previous drain of the patient.

A method for producing fluid for PD is explained with reference to the flowchart in FIG. 3. The method as described in the flowchart of FIG. 2 may be performed before the method described in FIG. 3. The method may be performed using any of the herein described systems 1. Before the method starts, the system 1 is connected to a source of water 7, e.g., via a hose to a tap, to the water connector 7a. The drain connector 12a is connected to a drain or to a drain bag for collecting used water. The outlet connector 5a is connected to the fluid line 5. Dedicated bags with PD-concentrates are connected to the PD-concentrate connectors 3a, 3b. The water may come directly from the tap, which is regarded as "raw water". The method may then pretreat the raw water before it is further used. In other words, the method at S2 comprises pretreating the water received via the water connector 7a before it is passed to the FO-unit 6. Alternatively, the water has already undergone a pretreatment, and can be directly supplied to the FO-unit 6. The pretreatment may include the removal of large particles, for example, using a sediment filter, and/or the removal of chlorine and variants thereof such as chloramine, etc., using a mixed-bed. In any case, the method at S3 comprises directing the (pre-treated) water into the feed side 6b of the FO-unit 6. The water is directed to the feed side using, e.g., valves (not shown in FIG. 1). The water is pumped to and through the feed side 6b using the second pump 42. At the same time, the method at S4 comprises directing one or more PD-concentrate fluids into the draw side 6a of the FO-unit 6.

In one embodiment, a PD-concentrate fluid using one or more buffer agents is used as a draw solution. This PD-concentrate fluid may be provided in the first PD-concentrate bag 4a. The PD-concentrate fluid with one or more buffer agents is then directed into the draw side 6a (e.g. using valves, not shown in FIG. 1), and pumped using the first pump 41. Alternatively, the draw solution is a mix of two different PD-concentrate fluids. In an example, the first PD-concentrate bag 4a provides a fluid with one or more buffer agents and/or electrolytes, while the second PD-concentrate bag 4b provides a solution with one or more osmotic agents. The draw solution is then a mix of the fluids from the first and second bags 4a, 4b. These fluids are then directed and pumped to the container 9 before it is used as a draw solution in the FO-unit 6. Still alternatively, the draw solution is a pre-diluted one or more PD-concentrates that has been pre-diluted using effluent from the patient. In any case, the method comprises directing one or more PD-concentrates into the draw side 6a of the FO-unit 6. The FO-unit 6 produces a diluted PD-concentrate.

The method at S5 senses a concentration of the diluted PD-concentrate fluid. The sensed concentration determines for example when the PD-concentrate has been sufficiently diluted, when the diluted PD-concentrate fluid is properly mixed, or when a final PD-solution has been produced. In some embodiments, the method at S6 comprises directing the diluted PD-concentrate fluid into a container 9. The method may comprise recirculating the diluted PD-concentrate in the first recirculation fluid path 61, including the container 9, until the concentration has reached a concentration that satisfies a concentration of the one or more PD-concentrates for a final PD-fluid. That is, the method at S7 may comprise controlling the degree of dilution by recirculating the diluted concentrate fluid in the first recirculation fluid path 61 including the draw side 6a of the FO-unit 6 and the container 9, until the one or more predetermined criteria are fulfilled. During recirculation, the diluted PD-concentrate continues to draw water from the feed solution and becomes increasingly diluted. This recirculation continues until one or more criteria is fulfilled. When the concentration of diluted PD-concentrate fulfills one or more criteria at S7c, the method may include collecting the diluted PD-concentrate in the container 9 or directing at S12 the diluted PD-concentrate fluid to the outlet connector 5a.

If only a solution with buffer and/or electrolyte agent(s) has been used as draw solution, the method at 510 comprises supplying a PD-concentrate fluid comprising osmotic agent(s) to the diluted PD-concentrate solution. A predetermined amount of PD-concentrate fluid comprising osmotic agent(s) may be supplied from the second PD-concentrate bag 3b into the container 9, or into the fluid path 2, e.g., into the second fluid line 22, from a source of osmotic agent to achieve a prescribed concentration of the osmotic agent in the diluted PD-concentrate fluid. The method may thereafter include directing the diluted PD-concentrate fluid to the outlet connector 5a. If the PD-concentrate fluid comprising osmotic agent(s) has been used as a draw solution together with the PD-concentrate fluid with buffer agent(s), the method may include directing the diluted PD-concentrate fluid to the outlet connector 5a, without directing the diluted PD-fluid via the container 9. In other words, if the concentration of the diluted PD-concentrate fluid corresponds to a final degree of dilution for a PD-fluid, the method may include directing the diluted PD-concentrate fluid to the outlet connector 5a. If it does not, the method at S11 may supply additional PD-concentrate fluid from the one or more PD-concentrate sources 4a, 4b to accomplish the composition of the final PD-fluid.

The method at S7a may control the degree of dilution of the one or more PD-concentrate fluid by controlling a flow rate of the one or more PD-concentrate fluids to an inlet of the draw side 6a, and/or at S7b controlling the flow rate of water at an inlet of the feed side 6b. The flow rate of the one or more PD-concentrate fluids to an inlet of the draw side 6a is controlled, wherein with the third pump 43 or with the first pump 41. The reject flow rate of water from the feed side 6b is typically controlled with the second pump 42. Alternatively, the flow rate of water into the feed side 6b is controlled (the second pump 42 may then be arranged to the third fluid line 25. The amount of PD-concentrates in the desired composition PD-fluid is known in beforehand, as well as the concentration of the PD-concentrate(s). Thus, for each batch of final PD-fluid, the amount of PD-concentrate(s) to be supplied into the draw side 6a is known. In case the diluted PD-fluid is not recirculated, the one or more PD-concentrate fluids needs to withdraw the necessary water in a single pass to dilute the one or more PD-concentrates to a final dilution degree corresponding to a dilution degree of a prescribed PD-fluid. The sensed concentration will then be used as feedback to the first pump 41 (arranged as in FIG. 1) and optionally for the second pump 42 to adapt the speed of the pumps such that the concentration fulfils one or more criterion for final PD-fluid. If the PD-concentrate fluid comprising one or more osmotic agents is supplied to the diluted PD-concentrate fluid after the FO-session, then the criterion is that the concentration of the diluted PD-concentrate fluid is equal to, or close to, a concentration that matches a prescribed concentration of the diluted PD-fluid in a final PD-fluid. The target concentration of the PD-concentrate fluid from the first PD-concentrate bag 4a (in the final PD-fluid) may be a function of a target concentration of PD-concentrate fluid from the second PD-concentrate bag 4b (in the final PD-fluid). After the PD-concentrate fluid comprising one or more osmotic agents has been supplied to the diluted PD-concentrate fluid, the method may include directing the diluted PD-fluid, now including the one or more osmotic agents, through the draw side 6a, or into a bypass line passing by the draw side 6a, or into a mixing chamber (not shown), to ensure a uniformity of the solution, and thus a homogenous solution. The method may ensure uniformity by sensing the concentration and monitoring that the concentration of the diluted PD-concentrate fluid is within a concentrate interval for a certain time period. The diluted PD-concentrate fluid is thus now a ready PD-fluid.

The used water in the FO will become enriched and thus more concentrated. The method may include directing the used water to a drain, recirculating the used water to be used again, or at S8 directing the used water downstream the FO-unit 6 to a water container 12, or a combination thereof. The water may thus be used in a single-pass, so that, new water is always used in the FO. Alternatively, a predetermined amount of water is used and recirculated, which is directed to drain after the FO is finished or collected in a water container, so it can be used for a forthcoming FO-session. In a still further embodiment, the main part of the used water is recirculated, some used water is directed to drain, and some new water is introduced. Thus, in some embodiments, the method at S7 includes controlling the degree of dilution by recirculating the water in the second recirculation fluid path 62, which includes the feed side 6b of the FO-unit 6a, until the one or more predetermined criteria are fulfilled.

In order to provide a final PD-fluid that can be directly introduced into the peritoneal cavity of a patient, the method may include heating the fluid in the fluid path 2 with a heater 52 (FIGS. 4 to 8). The heater 52 may also be used for disinfecting the fluid path 2 of the system 1.

Figures 4, 5:
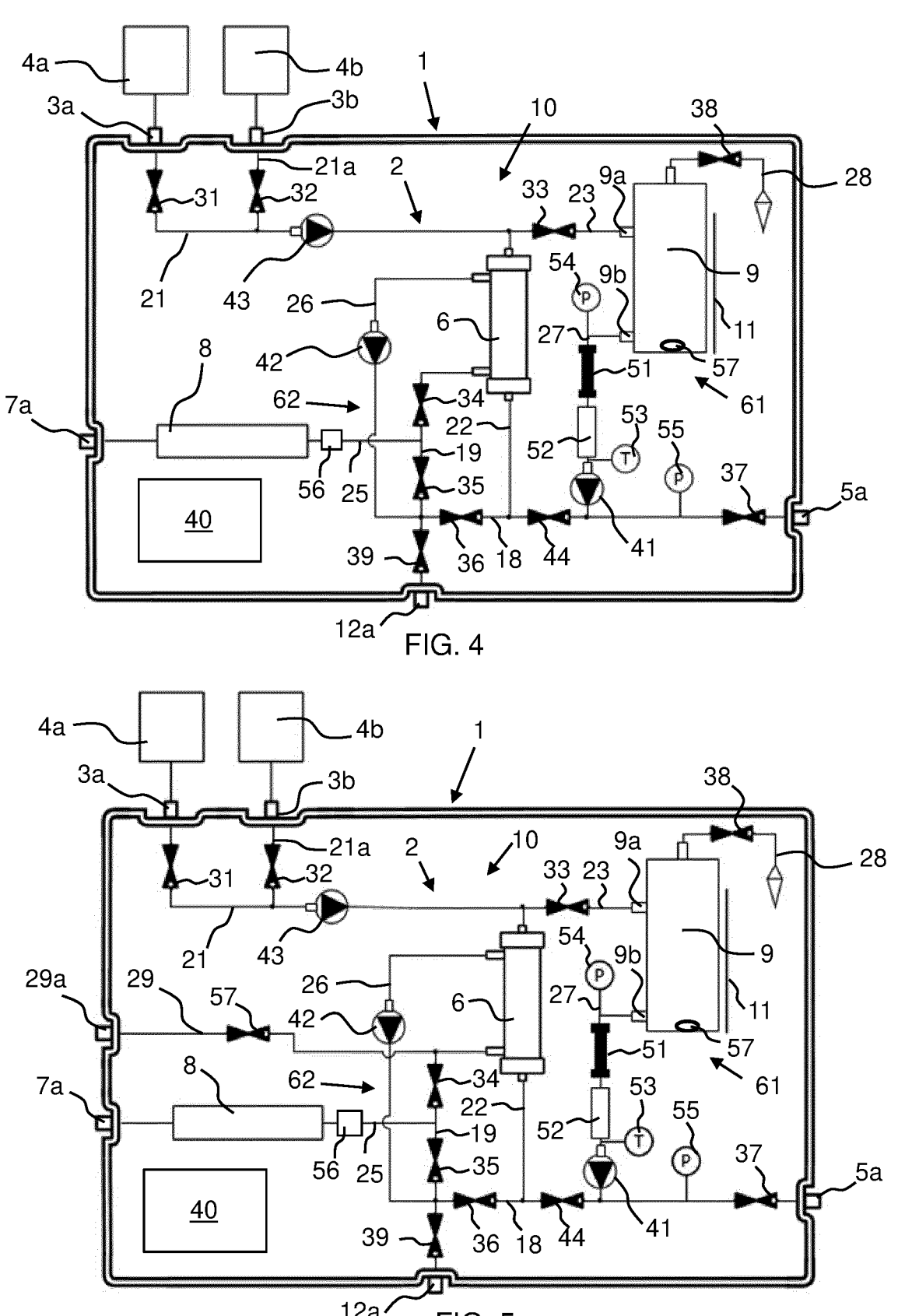
Figure 6:
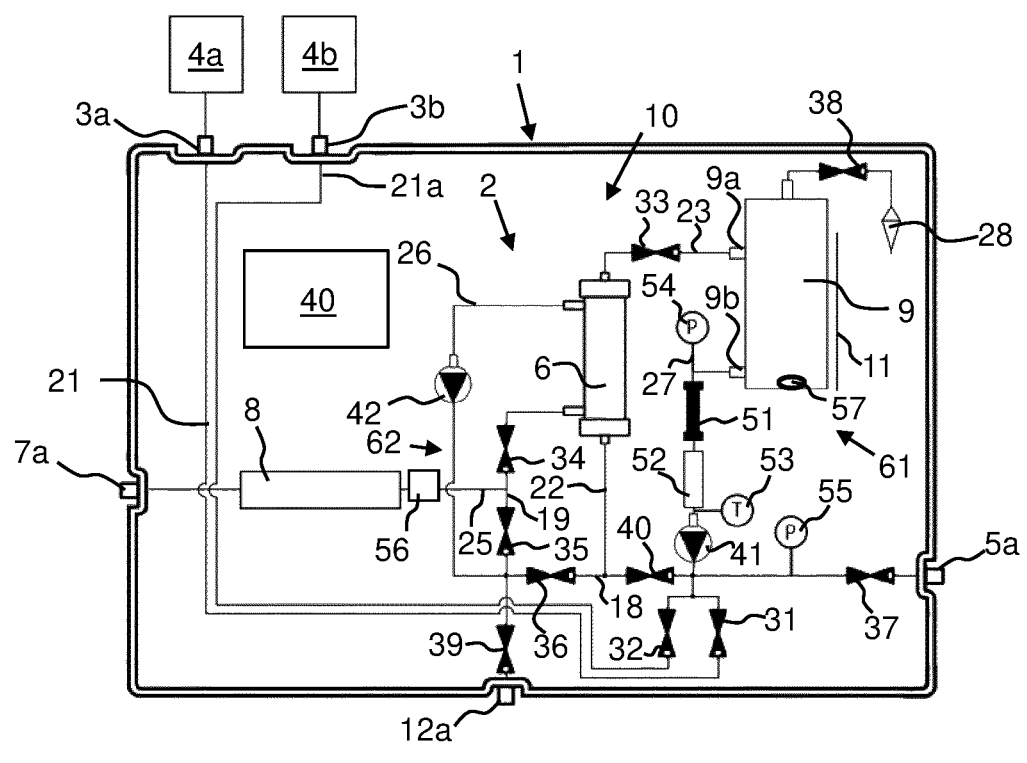

Different APD systems 1, which use FO to purify water and at the same time dilute PD-concentrate fluids, are now described. FIG. 4 illustrates a system 1 with batch-wise PD-fluid production. FIG. 5 illustrates the same system as in FIG. 4, with the addition of the capability to use effluent as feed solution to pre-dilute the PD-concentrates. FIG. 6 illustrates a system 1 in which PD-concentrate from both the first PD-concentrate bag 4a and the second PD-concentrate bag 4b can be introduced in the second fluid line 22, such that the one or more PD-concentrate fluids can be pumped with the first pump 41, to the container 9. References that are the same throughout the figures may not be repeated textually but include all structure, functionality and alternatives that have been described in connection with the references.

The system 1 in FIG. 4 is explained together with proposed sequences for producing fluid for PD, including diluted PD-concentrate fluid and final PD-fluid. The system 1 has the same references for the same parts as in the system in FIG. 1. In addition, the system comprises a third pump 43 (shown in phantom in FIG. 1) configured to control a flow rate of the one or more PD-concentrate fluids in the first fluid line 21. The first fluid line 21 is also provided with a first valve 31 arranged to operate with the first fluid line 21 upstream a connection point of the fluid line 21a to the first fluid line 21. A second valve 32 is arranged to operate with the fluid line 21 upstream the same connection point of the fluid line 21a to the first fluid line 21. The third pump 43 is arranged to operate with the first fluid line 21 downstream the same connection point. A third valve 33 is arranged to operate with the sixth fluid line 23. The sixth fluid line 23 is arranged between a first port 9a of the container 9 and the first fluid line 21. A fourth valve 34 is arranged to operate with the third fluid line 25 downstream the pretreatment unit 8, between the pretreatment unit 8 and an inlet to the feed side 6b. A fifth valve 35 is arranged to the seventh fluid line 19 between a connection point to the third fluid line 25 and a connection point to the fourth fluid line 26. A tenth fluid line 18 is arranged between the seventh fluid line 19 and second fluid line 22. A sixth valve 36 is arranged to operate with the tenth fluid line 18. A seventh valve 37 is arranged to operate with the second fluid line 22 close to the outlet connector 5a. An eight valve 38 is arranged to operate with a pressure relief line 28 from the container 9. A ninth valve 39 is arranged to operate with the seventh fluid line 19 downstream the connection point of the seventh fluid line 19 to the fourth fluid line 26 and the tenth fluid line 18. The ninth valve 39 controls the flow to the drain connector 12a.

The fifth fluid line 27 is fluidly connected to the second fluid line 22 and a second port 9b of the container 9. Thus, the fifth fluid line 27 connects the second fluid line 22 and the second port 9b of the container 9. A tenth valve 44 is arranged to operate with the second fluid line 22 between the connection point to the tenth fluid line 18 and a connection point to the fifth fluid line 27. The first pump 41 is arranged to operate with the fifth fluid line 27, instead of to the second fluid line 22 as in the system of FIG. 1, to pump fluid to or from the container 9. A heater 52 is arranged to operate with the fifth fluid line 27 between the container 9 and the first pump 41, but may alternatively be arranged to heat fluid at another location in the fluid path 2. A temperature sensor 53 is arranged to sense the temperature of the fluid in the fifth fluid line 27 downstream the heater 52. The concentration sensor 51 is here arranged to sense the concentration of the fluid in the fifth fluid line 27, here between the first pump 41 and the container 9.

A first pressure sensor 54 is arranged to sense the pressure in the fifth fluid line 27 between the first pump 41 and the container 9. A second pressure sensor 55 is arranged to sense the pressure in the second fluid line 22, which is the pressure of the final PD-fluid that is supplied to the outlet connector 5a. A level sensing arrangement 11 is arranged to sense the fluid level in the container 9. The level sensing arrangement 11 comprises for example an analogue level sensor. The control arrangement 10 is configured to control the diluted PD-concentrate fluid in the first recirculation fluid path, until the volume of the diluted PD-concentrate fluid fulfils a volume criterion. The volume of diluted PD-concentrate may be sensed with the level sensor or determined by means of the number of pump strokes performed with the volumetric first pump 41. An ultraviolet (UV) lamp 57 may be arranged inside the container 9 to disinfect the container 9. A water conductivity sensor 56 is arranged to sense the conductivity of the water downstream the pretreatment unit 8.

A proposed sequence, using the system 1 in FIG. 4, comprises one or more of the following steps:

1. Starting tap water pretreatment. The water connector 7a is connected to a source of tap water, e.g., via a hose. During this step, the valves 31, 32, 33, 34, 36, 37, 38 and 44 are closed, while valves 35 and 39 are open. The water is then pretreated in the pretreatment unit 8 and the conductivity is sensed with the water conductivity sensor 56.

2. Dosing the entire batch amount of PD-concentrate fluid from first PD-concentrate bag 4a volumetrically to the container 9. During this step, the valves 32, 34, 35, 36, 37 39, 44 are closed, and the valves 31, 33, 38 are open. The third pump 43 pumps PD-concentrate from the first PD-concentrate bag 4a. The level sensing arrangement 11 senses the level in the container 9.

3. Dosing the entire batch amount of PD-concentrate fluid from second PD-concentrate bag 4b volumetrically to the container 9. During this step, the valves 31, 34, 35, 36, 37, 39, 44 are closed, and valves 32, 33, 38 are open. The third pump 43 pumps PD-concentrate from the second PD-concentrate bag 4b. The level sensing arrangement 11 senses the level in the container 9.

4. Priming FO-filter with water, including pumping pretreated tap water through the FO-filter. During this step, the valves 31, 32, 33, 35, 36, 37, 38 and 44 are closed, while valves 34 and 39 are open. The water is pretreated in the pretreatment unit 8, the conductivity is sensed with the water conductivity sensor 8, and the pretreated water is pumped with the second pump 42 through the feed side 6b and out through the drain connector 12a.

5. FO/mixing session. Pretreated tap water is pumped through the FO-unit 6. The flow rate pumped with the second pump 42 will be the reject flow that is passed to drain connector 12a. The first pump 41 is run forward to recirculate the fluid in the container 9 via first the FO-unit 6, via the third valve 33 and then back to the container 9. The level sensing arrangement 11 and the conductivity sensor 51 are monitoring the FO-session (including mixing) with respect to volume and composition development of the evolving PD-fluid. Continue with the FO-session until target concentration, e.g., target conductivity, is reached. The target concentration of the diluted PD-concentrate from the first PD-concentrate bag 4a is calculated based on target osmotic agent concentration in the final PD-fluid. During this session, the valves 31, 32, 35, 36 and 37 are closed, while valves 33, 34, 38, 39 and 44 are open. The water is pretreated in the pretreatment unit 8, the conductivity of the pretreated water is sensed by the water conductivity sensor 56, the second pump 42 provides a water flow into the feed side 6b, the first pump 41 provides a flow rate into the draw side 6a, the level sensing arrangement 11 is sensing the level in the container 9, and the conductivity sensor 51 is sensing the conductivity.

6.
   a. Transmembrane pressure relieving. Due to the remaining concentration gradient between the water side (feed side 6b) and the PD-fluid side (draw side 6a) of the FO-unit 6, a significant transmembrane pressure may build if the sides stay stiffly separated. This pressure may harm the FO-unit 6 or the fluid path surrounding it. By opening the draw side 6a to drain and the feed side to the pretreatment, the concentration difference between the feed side and the draw side evens out sufficiently to allow closing to drain without the risk of transmembrane pressure building too high. During this step, the valves 31, 32, 33 35, 37 and 38 are closed, while valves 34, 36, 39 and 44 are open.

b. Alternatively to 6a, the transmembrane pressure relieving can be achieved by introducing diluted concentrate to the feed side of the FO unit to increase its concentration and thereby slow down the water extraction process. This serves two purposes; the dilution process is slowed down and may be better controlled to reach the target dilution while recirculation is maintained and transmembrane pressure build is avoided as the water extraction process is finally stopped. Introducing diluted concentrate to the feed side may be performed via valves 34, 35, 36 by pump 41 and/or by FO expansion of the draw volume trapped between valves 33 and 34. Alternatively, effluent can be introduced for the same purpose (FIG. 5). Fine tuning of the water extraction may be achieved by controlling the amounts of diluted concentrate, effluent and pretreated water on the feed side.

7. Delivering PD-fluid. When the concentration has reached the desired concentration, the PD-concentrate fluids have become so diluted that the diluted PD-concentrate fluid has a concentration as a PD-fluid, and is now referred to as final PD-fluid. During this step, the valves 31, 32, 33, 34, 35, 36, 39, 44 are closed, and valves 37, 38 are open. The first pump 41 provides a flow of PD-fluid from the container 9 to the outlet connector 5a, and the pressure is sensed with the second pressure sensor 55.

8. Draining the FO-unit 6. Draining the FO-unit 6 to the container 9 may be performed by pumping the first pump 41 in a reverse direction. During this step, the valves 31, 32, 34, 35, 36, 37, 38, 39 are closed, and the valves 33, 44 are open. The first pump 41, and the first pressure sensor 54 are operational. Alternatively, step 8 may be performed prior to step 7 to deliver also the PD fluid volume on the draw side. In general, the steps are not required to be performed in the order listed.

9. Draining container 9. Container 9 may be drained by running the first pump 41 in a forward direction. During this step, the valves 31, 32, 33, 34, 35 and 37 are closed, while valves 36, 38, 39 and 44 are open.

10. Steps 2 to 9 are repeated at least one time.

The proposed system 1 may be used to provide PD-fluid to a patient, to a PD-cycler or to a PD fluid container. The heater 52 may be used to heat disinfect the system 1 including the FO-unit 6 and the FO-membrane 6c. This enables reuse of the FO-membrane 6c.

FIG. 5 illustrates system 1 as in FIG. 4, with the addition that it also comprises an eighth fluid line 29 connected between an inlet connector 29a and the third fluid line 25, between the inlet port of the feed side 6a and the fourth valve 34. The eighth fluid line 29 thus fluidly connects the inlet connector 29a and the inlet port of the feed side 6a. An effluent line may be connected to the inlet connector 29a and be arranged to pass effluent from a patient into the inlet connector 29a. The effluent may then be used as a feed solution as has been previously described in relation to the flow chart in FIG. 2. Water extraction from the effluent is then performed as a first step to pre-dilute the PD-concentrate as much as possible. Raw water FO can be used to continue the dilution until PD-fluid composition is reached.

FIG. 6 illustrates a system 1 with an alternative arrangement of the first fluid line 21 and the fluid line 21a. In this embodiment, the first fluid line 21 is also connected to a connection point between the second fluid line 22 and the fifth fluid line 27. Fluid line 21a is connected to the same connection point between the second fluid line 22 and the fifth fluid line 27. The PD-concentrate(s) may then be supplied to the container 9 by operating the first pump 41 backwards. The PD-concentrate(s) are then used as draw solution as explained in the foregoing, by operating the first pump 41 in a forward direction. In some embodiments, PD-concentrate fluid from the first fluid bag 4a is supplied to the container 9 by operating the first pump backwards. The PD-concentrate fluid from the first fluid bag 4a is then used as draw solution and becomes diluted. When the diluted PD-concentrate fluid reaches a predetermined concentration, it can be collected into the container 9. The first pump 41 may thereafter supply a predetermined amount of PD-concentrate from the second fluid bag 4b by operating the first pump 41 backwards. The fluid in the container 9 may now be mixed by recirculating the fluid in the first recirculation fluid path 61 until a mixing criterion is fulfilled. The mixing criterion may include that the concentration has a value within a predetermined interval for a certain time. Alternatively, a mixing chamber (not shown) is fluidly arranged to the second fluid line 22 between the fifth fluid line 27 and the outlet connector 5a. The fluid may then be mixed in the mixing chamber on its way to the outlet connector 5a.

The proposed sequence described above produces PD-fluid batch-wise. The system 1 may also be used to produce PD-fluid online with the one or more PD-concentrates and FO purified water. The basic principle of diluting the PD-concentrates to a nominal PD-fluid composition is the same as in the proposed sequence, but the control mechanism to produce the PD-fluid is different. Instead of recirculating the evolving batch of diluted P-concentrate fluid until enough purified water has been extracted from the water at the feed side, the correct amount of water extraction (concentrate dilution) is achieved during a single pass of the one or more PD-concentrates through the FO-unit 6. This can be accomplished if one or several of the parameters controlling the water extraction rate are controlled. These parameters include, but are not limited to:

1. A pressure difference between the feed side 6b and the draw side 6a of the FO-unit 6.
2. Temperature representing the temperature of the fluid at the feed side 6b and/or the draw side 6a.
3. A water side osmolarity (the reject flow rate).
4. The PD-concentrate flow rates.

The PD-concentrate flow rates will determine the PD-fluid production rate and should thus not be used for water extraction rate control if the production flow rate of PD-fluid to the outlet connector 5a, e.g., be controlled by the user or by pressure feedback. The feedback mechanism used to control the water extraction rate influencing parameters can be, e.g., concentration (conductivity). The above-mentioned parameters may also be used for controlling the water extraction rate for producing PD-fluid batch-wise.

Water extraction from raw water (e.g., tap water) can be performed until the osmolarity of the water reaches a point at which the osmotic pressure between the feed side 6b and draw side 6a is close to zero and further water extraction is no longer possible. The reject flow is thereby minimized, which means that the tap water consumption is minimized. This can be achieved in several ways. In one embodiment, online production of PD-fluid is performed, wherein the feed and draw solutions are supplied in counter-current flows in the FO-unit 6, while controlling the flow rates of the draw- and feed solutions, to reach a PD-fluid composition at the draw side outlet and close to PD-concentrate osmolarity on the feed side outlet.

In another embodiment, batch production of PD-fluid is performed. Here, during a first batch, a fresh tap water volume is recirculated in the second recirculation fluid path 62, and a PD-concentrate fluid volume is recirculated in the first recirculation fluid path 61 until PD-fluid composition is reached on the draw side 6a. If the initial tap water volume is optimized, its osmolarity at the end of the batch production can be maximized (to be close to that of the PD-fluid on the draw side 6a). During the second batch, and forthcoming batches, the remaining water volume (with close to PD-fluid osmolarity) may be reused for water extraction during the initial phase of the second batch production since the draw solution is then highly concentrated. This can bring the water osmolarity up even further before it is rejected. An optimized volume of fresh tap water is then introduced and recirculated to finalize that batch production. The water consumption may thus be minimized by maximizing the reject water osmolarity. Depending on the FO-membrane properties, the acceptable reject water osmolarity may be limited by water side fouling and/or the forward flux of compounds concentrated on the water side. Recirculating water on the feed side has the potential advantage of decreased fouling risk due to increased bulk flow along the membrane.

Figure 7:
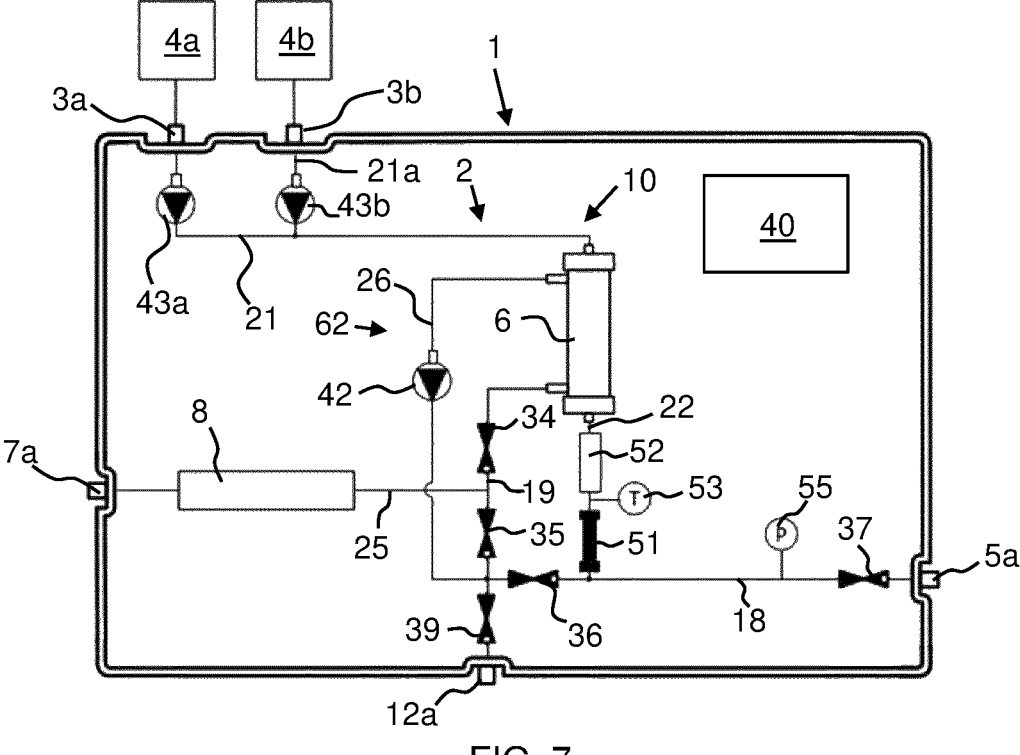
Figure 8:
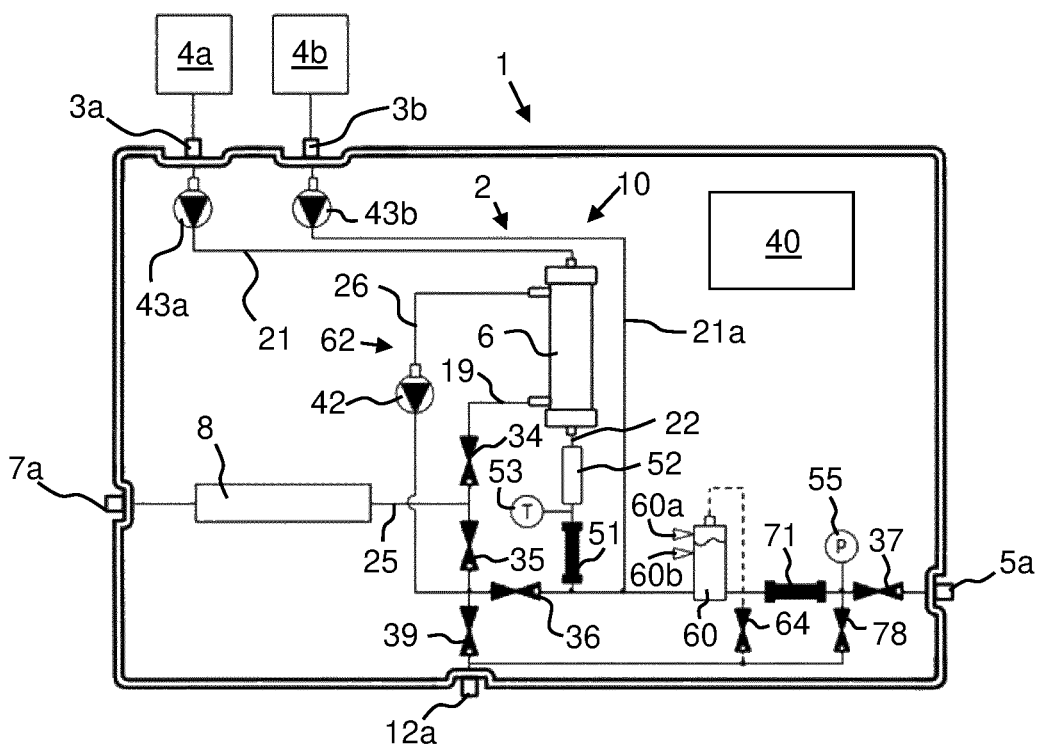

System 1 of FIGS. 7 and 8 illustrate alternative embodiments, which are online embodiments that produce a final PD-fluid that is delivered directly to the patient or for collection for later use in a storage container. The fluid is in FIGS. 7 and 8 is not mixed in container 9, as is done in FIGS. 1 (as an alternative) and 4 to 6. FIGS. 7 and 8 include many of the same components including first PD-concentrate fluid 4a, e.g., buffer concentrate, and second PD-concentrate fluid 4b, e.g., osmotic agent or glucose concentrate, which are connected respectively to system 1 via PD-concentrate connectors 3a and 3b. In FIGS. 7 and 8, a separate third or concentrate pump 43a and 43b is provided for each PD-concentrate fluid 4a, 4b. Forward osmosis (FO) unit 6 including a draw side and a feed side is also provided. The feed side of FO-unit 6 is part of a feed side recirculation fluid path 62, which also includes second or feed side pump 42 operable with fourth fluid line 26 and valves 34 and 35. A concentration, e.g., conductivity, sensor 51, temperature sensor 53 and heater 52 are provided at the outlet of the draw side of FO-unit 6. Concentration, e.g., conductivity, sensor 51, and temperature sensor 53 output to control unit 40, which uses the conductivity reading as feedback, while control unit 40 causes one or more concentrates to be increasingly added or diluted until a desired conductivity is reached. Control unit 40 uses the temperature reading as a compensation factor for the conductivity reading and as feedback for controlling an amount of power applied to heater 52 to achieve a desired final PD-fluid temperature, e.g., body temperature of 37° C.

The alternative embodiments of system 1 in FIGS. 7 and 8 also include pretreatment unit 8 (which may include some or all structure, functionality and alternatives discussed herein) for pretreating water entering system 1 via water connector 7a. Water leaving pretreatment unit 8 flows either (i) via valves 35 and 39 to drain via drain connector 12a or (ii) via valve 34 to the feed side of FO-unit 6. Control arrangement 10 in both FIGS. 7 and 8 is configured so that it may pull in additional pretreated water from pretreatment unit 8 into the feed side and/or one (FIG. 8) or both concentrates (FIG. 7) from sources 4a and/or 4b into the draw side, wherein the pretreated water osmoses across the FO-membrane to dilute the one or more concentrate 4a and/or 4b. The FO-membrane also further filters and purifies the water, making or ensuring that it is suitable for PD treatment.

FIGS. 7 and 8 also include an outlet valve 37, outlet connector 5a and pressure sensor 55 for controlling patient pumping pressure. Pressure sensor 55 outputs to control unit 40, which uses the pressure reading as feedback to control the speed of at least one of pumps 42, 43a and 43b so as to set the outlet pumping pressure to the patient at a safe level, e.g., 0.21 bar (three psig) or less.

The differences between system 1 of FIGS. 7 and 8 include how the PD-concentrate fluids 4*a* and 4*b* are introduced. In FIG. 7, both PD-concentrate fluids 4*a* and 4*b* (e.g., buffer and glucose) are pumped into the draw side 6*a* of FO-unit 6. Here, both diluted concentrate fluids are monitored by concentration or conductivity sensor 51 for feedback to bring the final PD-fluid to a desired concentration or conductivity. The parameters that are controlled via the feedback from concentration or conductivity sensor 51 include any one or more of the speed of concentration pumps 43*a* and 43*b* and the speed of second or feed side water recirculation pump 42.

In FIG. 8, only first PD-concentrate fluid 4*a* (e.g., buffer) is pumped into the draw side of FO-unit 6, which is monitored by concentration or conductivity sensor 51 for feedback to bring the PD-fluid to a desired concentration or conductivity level for the first PD-concentrate fluid (e.g., buffer). Second PD-concentrate fluid 4*b* (e.g., glucose) is pumped instead into tenth fluid line 18 downstream from FO-unit 6. Second PD-concentrate fluid 4*b* is mixed with the properly diluted first PD-concentrate fluid 4*a* in a mixing chamber 60. Mixing chamber 60 may be a smaller container (e.g., 50 to 100 ml, which is smaller than container 9) and operate with a pair of level sensors 60*a* and 60*b* that output to control unit 40, which uses the outputs to maintain a level of PD-fluid in mixing chamber 60 that is somewhere between the sensors. The fluid also mix in tenth fluid line 18, such that mixing chamber may not be needed, e.g., as in FIG. 7. Mixing chamber 60 also acts as an gas separation chamber or gas trap and may accordingly be provided in any of the embodiments of system 1 discussed herein for further mixing and/or gas separation. Gas or PD-fluid may be vented from the top of mixing chamber 60 to drain connector 12*a* via a vent valve 64.

In FIG. 8, after the second PD-concentrate fluid 4*b* is mixed with diluted first PD-concentrate fluid in mixing chamber 60, final PD-fluid is pumped past a second or final concentration or conductivity sensor 71, which outputs to control unit 40. Control unit 40 interrogates the output from final conductivity sensor 71 to ensure that the final PD-fluid has a desired final concentration or conductivity. If so, control unit 40 causes seventh or outlet valve 37 to open, allowing properly mixed and heated final PD-fluid to be pumped to the patient, to a cycler or to a storage container or bag, at a safe pumping pressure. If not, control unit 40 causes bypass valve 78 to open, allowing the improperly mixed PF-fluid to be delivered to drain connector 12*a*.

As discussed above, the speed of at least one of pumps 43*a*, 43*b* and 42 is controlled via control unit 40 so as to deliver final PD fluid to the patient at both a desired concentration or conductivity (via feedback from sensors 51 and possibly sensor 71) and a desired pressure (via feedback from pressure sensor 55). Thus there are two feedback loops for each pump 43*a*, 43*b* and 42 that is controlled via feedback (one or more of the pumps may be operated at a set speed). To keep the feedback loops from conflicting, it is contemplated for control unit 40 to set maximum speeds to ensure that a patient pressure limit is not exceeded and to control the pumps within those maximum speeds to achieve the desired concentration or conductivity. That is, the feedback loop for concentration or conductivity is dependent on the feedback loop for pressure because the pressure loop sets the speed limits within which the concentration or conductivity feedback loop may vary the speeds for concentration or conductivity control. The above is true when final PD fluid delivery flow is pressure controlled (e.g. when delivering directly to a patient). When delivering to a cycler or fluid container instead, for example, a fixed delivery flow may be set and it is then only the concentration feedback loop that is active.

For any of the versions of system 1, the flow rates created by second or feed side pump 42 and third or concentrate pump 43 depend on the water volume available and time available for water extraction. Lower flow rates for these pumps increase the extraction efficiency. The flow rates for pumps 42 and 43 also depend on the size of the FO-unit 6. A larger surface area for the unit increases the efficiency, which may allow for higher flow rates. Overall, it is the combination of raw water or effluent flow rate, concentrate flow rate and membrane surface area that determines the efficiency.

In an example for system 1, forty minutes is needed for effluent extraction and mixing, yielding an effluent flow rate at or above 75 ml/min. Referring again to FIG. 1, if instead a large amount of effluent (e.g., 8 to 10 liters) can be saved in effluent source 30*a*, and 8 to 10 liters of diluted concentrate is stored in container 9, then a longer FO session would be allowed, yielding around a 15 ml/min effluent flow rate. Such an FO session may be performed during treatment and during the daytime without other activities.

System 1 may, in a first phase, extract water from effluent in a very efficient way (by for example lowering the effluent flow or adding transmembrane pressure (TMP)) to produce a diluted PD concentrate. System 1 may, in a second phase, use a small volume of, for example, tap water to further dilute the diluted concentrate into a finally diluted concentrate. The tap water consumption is thereby minimized and there is no need for a permanent tap connection. Instead the patient can add a small volume (e.g., one liter per treatment) of tap water into a water tank (not illustrated) prior to treatment. The water tank is then the source of water and connected to the water connector 7*a*. The water extraction from the effluent performed in the first phase can be run on the effluent volume from the previous drain during the current dwell. Also, the efficiency of the water extraction from the effluent (and thereby the tap water savings) can be maximized if a large amount of effluent (e.g. 8 to 10 liters) can be saved in effluent source 30*a*, and 8 to 10 liters of diluted concentrate is stored in container 9, then a longer FO session would be allowed, yielding around a 15 ml/min effluent flow rate. Such an FO session may be performed during treatment and during the daytime without other activities.

It is also contemplated for any version of system 1 described herein to maintain a transmembrane pressure gradient between the feed side 6*b* and the draw side 6*a* of FO-unit 6, wherein the feed side pressure is greater than the draw side pressure. Doing so increases the water extraction efficiency of FO-unit 6. The transmembrane pressure gradient or ΔP may be anywhere above zero bar to four bars (58 psig) or higher depending on the specifications and/or requirements of the manufacturer of FO-unit 6. One way to create a higher feed side pressure is to move second pump 42 in FIG. 1 to third fluid line 25 so that positive fluid pressure is instead applied to the feed side 6*b* of FO-unit 6. Controlling the speed of second pump 42 thereby controls feed side pressure. Alternatively or additionally, a variable flow restrictor (not illustrated) under control of control unit 40 may be added to operate with fourth fluid line 26. Control unit 40 here causes the variable flow restrictor to partially occlude line 26, creating an increased backpressure in the feed side of FO-unit 6. Second pump 42 and the flow restrictor may be referred to herein as a pressurization device. The pressure gradient may be caused alternatively or additionally by lowing the pressure on the draw side 6a of FO-unit 6. It is contemplated to lower the draw side pressure hydrostatically by structuring system 1 so that diluted PD concentrate container 9 resides elevationally low relative to FO-unit 6.

It may be possible to increase extraction efficiency alternatively or additionally by heating or increasing the temperature of FO-unit 6. For example, if it is desirable to have a higher FO-unit 6 temperature, an additional or alternative heater, e.g., pre-heater (not illustrated), may be placed along effluent fluid line 25, which heats or increases the temperature FO-unit 6. The increased effluent temperature may for example be anywhere from slightly higher than ambient temperature to 50° C. or perhaps higher depending on the manufacture of the FO-unit. The temperature to which the effluent is heated is selected so that FO-unit 6 is in turn heated to a desired level, and also so that the final PD fluid delivered to the patient may be set to be around body temperature or 37° C. It may be found that FO-unit 6 acts as a heat sink such that even if the effluent is heated to 50° C., the diluted concentrate leaving FO-unit 6 is less than 50° C., such that heating via downstream heater 14 is still needed. Fouling in effluent fluid line 25 is also a consideration in determining the temperature to which the effluent is heated because higher temperatures may increase fouling. The reason why an increase in extraction efficiency occurs by heating FO-unit 6 may be linked to an increased flux across FO-membrane 6c.

It is accordingly expressly contemplated for any version of system 1 discussed herein to manipulate, select or set any one or more of membrane surface area, feed side and draw side flow rates, pressure gradient ΔP or transmembrane pressure across the membrane, and/or the temperature of FO-unit 6 to achieve a desired exchange efficiency. Those variables are balanced against cost and ease of use to produce an overall desirable system 1.

Figure 9:
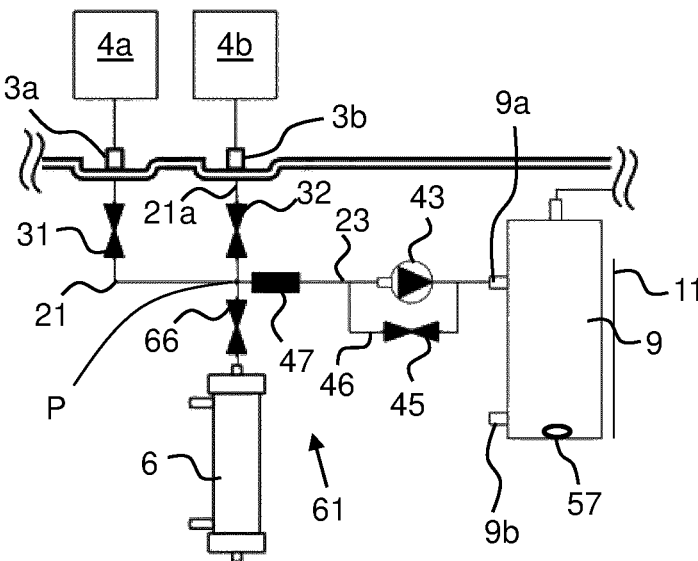

Referring now to FIG. 9, any of the versions of system 1 described herein may include structure to mitigate potential problems with controlling the dosing the concentrates. In particular, in FIGS. 1, 4 and 5 concentrate from container 4b may enter the stream of the concentrate from container 4a, which means that both concentrates carry a small amount of the other concentrate when added (or at least in one of the dosing steps). Also, the first time either concentrate is added there will be air in line 21 and/or lines 21a.

As a mitigation for the concentrate contamination issue, FIG. 9 leads each concentrate line 21, 21a to a common point P at which lines 21, 21a meet first recirculation fluid path 61. In this manner, each concentrate 4a, 4b has its own route to the first recirculation fluid path 61, wherein the recirculation path is part of the mixing volume. Additionally, third or concentrate pump 43 is moved into first recirculation fluid path 61, which allows pump 43 to add the amount concentrate that control unit 40 has been programmed to add (disregarding the stroke volume error of the pump) once concentrate lines 21, 21a have been filled. Further additionally, pump 43 is placed in parallel with a valve 45 under control of control unit via a loop 46 extending to either side of pump 43, so that the flow out of FO-unit 6 can be free during the dilution phase, that is, valve 45 enables free flow through recirculation fluid path 61. Control unit 40 in one embodiment causes pump 43 to run slowly during the dilution phase, so that at the end of the dilution phase, pump 43 and loop 46 are filled with the same fluid as is present in diluted PD concentrate container 9 and recirculation fluid path 61.

As a mitigation for the air entrainment issue, it should be noted that the severity of the air issue depends on the amount of unpurged air present in either concentrate 4a or 4b during the first batch preparation of PD fluid and the size of lines 21 and 21a leading to point P. In FIG. 9, an air/fluid sensor 47, e.g., capacitive or ultrasonic sensor, under control of control unit 40 is placed directly after point P. Control unit 40 causes pump 43, at least at the start of the first batch of PD fluid, to pump one of concentrates 4a, 4b until sensor 47 sees fluid and then to switch to the other concentrate 4a, 4b and do likewise. The volume in lines 21 and 21a and the portion of recirculation fluid path 61 leading to sensor 47 is known (or sufficiently known). Hence control unit 40 may determine the volumes of concentrates 4a and 4b pumped by counting the strokes pumped by pump 43 (assuming pump 43 is a piston or other accurate volumetric pump or is a less accurate pump in combination with a flow meter or scale).

While the invention has been described in connection with what are presently considered to be the most practical and preferred embodiments, it is to be understood that the invention is not to be limited to the disclosed embodiments, but on the contrary, is intended to cover various modifications and equivalent arrangements included within the scope of the appended claims.

The invention claimed is:

1. A system for producing fluid for peritoneal dialysis (PD), the system comprising:
   a fluid path including one or more PD-concentrate connectors each configured to be connected to one or more sources of PD-concentrate fluid, and a water connector configured to be connected to a source of water;
   a forward osmosis (FO)-unit including a draw side and a feed side separated by a FO-membrane, the FO-unit fluidly connected to the fluid path, wherein the FO-unit is configured to receive one or more PD-concentrate fluids at the draw side, and to receive water at the feed side, and wherein purified water is transported to the one or more PD-concentrate fluids through the FO-membrane by means of an osmotic pressure gradient between the draw side and the feed side, whereby the one or more PD-concentrate fluids is diluted to produce a diluted PD-concentrate fluid;
   a concentration sensor configured to sense a concentration of the diluted PD-concentrate fluid;
   a container fluidly connected or connectable to the fluid path, wherein the container is arranged to receive the diluted PD-concentrate fluid, and wherein the fluid path includes a first recirculation fluid path including the draw side of the FO-unit and the container; and
   a control arrangement configured to:
      control a degree of dilution of the one or more PD-concentrate fluids based on the sensed concentration and by recirculating the diluted PD-concentrate fluid in the first recirculation fluid path such that one or more predetermined criteria are fulfilled, and
      direct the diluted PD-concentrate fluid to an outlet connector while sensing a pressure, with a pressure sensor, of the diluted PD-concentrate fluid provided to the outlet connector for controlling the pressure of the diluted PD-concentrate fluid.

2. The system according to claim 1, wherein the one or more predetermined criteria includes at least one of: (i) the concentration of the diluted PD-concentrate fluid having a concentration that is at least substantially equal to a concentration that matches a prescribed concentration of the diluted PD-concentrate fluid in a final PD-fluid; (ii) the concentration of the diluted PD-concentrate fluid corresponding to a final degree of dilution for a PD-fluid; and/or (iii) the concentration of the diluted PD-concentrate fluid is being within a concentrate interval for a certain time duration.

3. The system according to claim 1, wherein the control arrangement is configured to control the degree of dilution of the one or more PD-concentrate fluids by controlling a flow rate of the one or more PD-concentrate fluids to an inlet of the draw side, controlling a flow rate of the water to an inlet of the feed side, and/or controlling a flow rate of reject water from an outlet of the feed side.

4. The system according to claim 1, further comprising a pump positioned and arranged to at least one of (i) deliver the diluted PD-concentrate fluid, or (ii) remove the diluted PD-concentrate fluid from the container along a line.

5. The system according to claim 4, further comprising at least one of (i) a fluid heater located along the line, (ii) a concentrate pump located in the first recirculation fluid path, wherein the concentrate pump is optionally placed in parallel fluidically with a valve, or (iii) an air/fluid sensor located in the first recirculation fluid path for determining when the one or more PD-concentrate fluids has reached the air/fluid sensor.

6. The system according to claim 1, wherein the fluid path includes a second recirculation fluid path including the feed side of the FO-unit, and wherein the control arrangement is configured to recirculate the water in the second recirculation fluid path until the one or more predetermined criteria are fulfilled.

7. The system according to claim 1, wherein the control arrangement is configured to direct the diluted PD-concentrate fluid to the outlet connector upon the one or more predetermined criteria being fulfilled.

8. The system according to claim 1, further comprising a water container configured to collect the water downstream from FO-unit.

9. The system according to claim 1, wherein the fluid path includes an osmotic agent connector configured to be connected to a source of osmotic agent and wherein the control arrangement is configured to supply an osmotic agent from the source of osmotic agent to the fluid path to achieve a prescribed concentration of the osmotic agent in the diluted PD-concentrate fluid.

10. The system according to claim 1, wherein the fluid path includes an inlet connector configured to be connected to a source of effluent and wherein the FO-unit is configured to receive the effluent at the feed side to transport water from the effluent to the one or more PD-concentrate fluids through the FO-membrane by means of the osmotic pressure gradient diluting the one or more PD-concentrate fluids and producing a pre-diluted PD-concentrate fluid, after which the pre-diluted PD-concentrate fluid is included in the one or more PD-concentrate fluids that the FO-unit is configured to receive.

11. The system according to claim 10, further comprising an effluent container fluidly connected or connectable to the fluid path, wherein the effluent container is arranged to receive the effluent from a patient.

12. The system according to claim 1, further comprising a pretreatment unit configured to pretreat the water received via the water connector before it is passed to the FO-unit.

13. The system according to claim 1, further comprising a pressurization device configured and arranged to create a higher pressure on the feed side of the FO-unit than the draw side.

14. The system according to claim 1, wherein the FO-membrane is configured to purify the water received at the feed side into the purified water.

15. A method for producing fluid for peritoneal dialysis (PD) in a system comprising a forward osmosis (FO)-unit including a draw side and a feed side separated with a FO-membrane, wherein the FO-unit is configured to receive one or more PD-concentrate fluids at the draw side, and to receive water at the feed side, and wherein purified water is transported to the one or more PD-concentrate fluids through the FO-membrane by means of an osmotic pressure gradient between the draw side and the feed side to dilute the one or more PD-concentrate fluids into a diluted PD-concentrate fluid, the method comprising:

directing the water into the feed side of the FO-unit;

directing the one or more PD-concentrate fluids into the draw side of the FO-unit;

sensing a concentration of the diluted PD-concentrate fluid;

directing the diluted PD-concentrate fluid into a container;

controlling a degree of dilution of the one or more PD-concentrate fluids during production of diluted PD-concentrate fluid based on the sensed concentration and by recirculating the diluted PD-concentrate fluid in a recirculation fluid path including the draw side of the FO-unit and the container such that one or more predetermined criteria are fulfilled; and direct the diluted PD-concentrate fluid to an outlet connector while sensing a pressure, with a pressure sensor, of the diluted PD-concentrate fluid provided to the outlet connector for controlling the pressure of the diluted PD-concentrate fluid.

16. The method of claim 15, wherein transporting the purified water through the FO-membrane further purifies the purified water.

* * * * *